US00PP13498P2

(12) United States Plant Patent
Monckton

(10) Patent No.: US PP13,498 P2
(45) Date of Patent: Jan. 21, 2003

(54) NARSISSUS PLANT NAMED 'CHARLES THATHAM'

(75) Inventor: Timothy James Monckton, 7, John Forbes House, Pittville Crescent, Cheltenham, Glos, GL 52 2Q7 (GB)

(73) Assignee: Timothy James Monckton, Cheltenham (GB)

( * ) Notice: Subject to any disclaimer, the term of this patent is extended or adjusted under 35 U.S.C. 154(b) by 0 days.

(21) Appl. No.: 09/504,095

(22) Filed: Feb. 15, 2000

(30) Foreign Application Priority Data

Jan. 19, 1993 (GB) ..... 5218

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Anne Marie Grünberg

(57) ABSTRACT

A new variety of Narsissus, sub genus Tazetta, generated as a result of either a sport (mutant) or a natural cross of unknown Narsissus species, and having the unique properties of being exceptionally early flowering (late October to early November) from an August planting outdoors, and also being moderately winter hardy with distinctly elegant scented flowers, with good propagative and yield characteristics.

3 Drawing Sheets

BACKGROUND OF THE INVENTION/DISCOVERY

This plant was discovered in a cultivated garden in Jersey, Channel Islands, UK by me some 9 years ago. It is probably the result of a natural cross or is a mutant (sport). The garden, which belonged to my late grandfather, contained many species of Narsissus. Since its discovery, after producing 5000 bulblets from tissue culture that took three years to grow to flowering bulb size, I have steadily multiplied the variety using the 'chipping' technique. The only stocks in the world are in Jersey.

The bulb is recognised by The Royal Horticultural Society in England as being a *Narsissus tazetta.*

BREIF SUMMARY OF THE DISCOVERY (INVENTION)

CHARLES THATHAM is a true autumn flowering hardy Narsissus when grown outdoors. When planted in August, it will emerge in mid September, and flower between late October and early November in the UK. It flowers earlier outdoors in a milder climate such as in the Channel Islands, and later in central England. However, if bulbs are planted late, ie; in mid Sept or October, it will flower later—ie; in late November—mid December, whether planted indoors or outside. Late planted indoor bulbs will flower much earlier than late planted outdoor bulbs. The flowers have a delightful and powerful scent. Bulbs, depending on their size, can produce between three and twelve florets per stem. Each floret opens in fairly quick sequence with the first to break out to open first. It takes on average 7 days between the first floret opening and the last floret opening. The florets fade in the same sequence as they emerged (broke out) over a period of three to four weeks if not cut. The scent is at its most pungent when the florets first open and reduces slowly. The bulb leaves emerge first in the autumn, and are the same length, or slightly shorter than the flowering stem at the start of flowering. They are erect up to and just after flowering. After flowering has completed, the leaves extend up to twice the length of the origonal flowering stem and gradually become more prostrate over the ground. The plant is very hardy, and in trials, has been subjected to temperatures of down to −15 degrees C. for up to three days at a time without any appreciable damage. Sometimes, with a wind chill factor, the tops of the leaves will scorch. On one occasion exposure to a wind chill factor of −22 degrees C. over five days, caused the leaves to be dessicated. However, the bulbs survived, and grew the following autumn.

Moderate frost, ie; down to −5 Degrees C. will sometimes cause the stems to lean, but this does not affect the flower, and the stem will soon come back errect after recovery in milder temperatures. The bulb leaf growth is very vigorous, and it does not scenese until well into May/early June—ie; the same time as spring flowering Narsissus species.

The most distinguishing feature of this plant, Charles Thatham, is that it flowers exceptionally early being naturally autumn flowering, as well as being winter hardy.

For successful outdoor propagation with high yields, this bulb needs an average mean winter temperature not less than 5 degree C. between 1$^{st}$ Nov and 1st April, without exposure to temperatures of minus 6 degrees C. for longer than 8 days in succession. However, it will propagate at lower mean winter temperatures, producing smaller bulbs.

BREIF DECSRIPTION OF THE DRAWING/ PHOTOS

The first picture is a photocopy of a painting of the whole plant flowering. This shows the plant as it would be in late October/early November as a flowering plant. Although most bulbs produce only one flowering stem, this drawing shows two flowering stems from one bulb that also occurs commonly with this bulb.

The second picture shows a photograph of a single flowering plant, including the leaves.

The third picture shows an enlarged photo of a group of flowers in full bloom, clearly defining the petal and corona shape and colour.

DETAILED BOTANICAL DESCRIPTION

This new and distinct variety of *Narsissus tazetta* plant is exceptionally early in autumn flowering and is uniquely winter hardy. It is different in floral color and shape than any outdoor autumn/late winter flowering Narsissus such as 'Soliel D'or' or 'White Narsissus' (U.S. Plant Pat. No. 3,366) to which it most closely resembles. 'White Narsissus' is clearly different from 'Charles Thatham' in that it has larger and more rounded shaped flowers, with a paler colored yellow corona. This plant is not winter hardy, and is grown predominantly as an indoor plant, flowering indoors in December from a late September planting.

'Soliel D'or' is a late autumn flowering plant grown outdoors in Cornwall in the UK. It is later flowering, and is clearly different in that it has larger flowers that have yellow petals, and a yellow corona.

A detailed description of the flowering plant which belongs to division 8 is as follows:

Flowers: There are 3–12 flowers (florets) per stem. The florets are 25–30 mm wide initially enclosed by a spathe or bract which later becomes brown (199D). There are 6 perianth segments that are broadly ovate or oblong, blunt, prominantly mucronate, creamy white (155C), spreading, with margins incurling, overlapping a quarter. The corona is cup shaped, mouth straight and 8 mm diameter, shallowly six lobed with a wavy entire rim and a bright yellow-orange (17B). The anther lobes are in two whorls of three, 3 mm long, the outer whorl with the top of the anther lobes level with the base of the corona, the inner whorl with the base of the anther lobes level with the base of the corona, dehiscing to release bright golden pollen (20A). The style is slender, extending to above the upper anther lobes but within the corona. The stigma is trifid and pale green (14d). The drawings and pictures do not necessarily show an exact duplication of these precise colour descriptions, above, which are correct and taken from real life flowers and plants. The flower and plant description used The Royal Horticultural Society Colour Chart. The plant flowers naturally very early—well before Christmas. In central England it flowers on average in the first week of November, but can be earlier in a warm south facing aspect. In the warmer Channel Islands and Cornwall it starts to flower during the start of the third week of October. The flowers are strongly scented, with the scent being distinctly sweeter than the indoor Narsissus Paper White, which has a musky scent. The plants used in this description are identical to all the other existing flowering stock of this plant, and the age of these plants is two years since prior chipping, being the offspring of the origonal stock bred from chipping in 1993.

Stem: The 6–10 mm diameter stem is the same colour as the leaves (137A), being strong round and dark green, and has a pale green 10 mm papery collar ajoining the junction of the cluster of florets and stem. The stem also tapers gradually towards the floret cluster, with a 30% reduction in diameter comparing the base of the stem and the neck of the stem. The stem reaches an average height of 200 mm, but can vary and can be 140 mm up to 250 mm, depending on light intensity, and plant density.

Leaves: Dark green (137A) and on average 15 mm wide, smooth but slightly ribbed, and gradually tapering to a point. They are the same length, or slightly shorter than the flower stem and errect at flowering, but gradually extent up to twice this length (between 300–400 mm) and often become prostrate after flowering has ceased. Thus leaves are on average 180 mm at flowering, but vary in length from 160 mm to 240 mm at flowering. Scenescence starts in late May, and is usually complete by mid June.

Bulbs: The bulbs are short necked. Flowering size bulbs range from 30 mm to 60 mm across the widest point of the bulb which is between 50 mm–80 mm in length. The skin covering the bulb is dark brown (174A), and wrinkled, tending to peel easily when very dry, exposing the creamy white flesh of the inner bulb. A full size flowering bulb will produce on average two bulblets per annum attached to the main bulb, which can be easily broken away. Bulblet size varys from 10 mm across the base to 30 mm across the base. These always produce autumn shoots (leaf) at least a week earlier than full sized mature flowering bulbs.

Flowering plant: At the start of flowering, the flowering stem and leaves are between 200 mm and 300 mm in height on average, but can be taller in low light intensity situations. The earliest flowering plants are always shorter than the later flowering plants. Although the bulb flowers on average in late October/early November, in certain conditions some may flower up to two weeks earlier, and often a very few bulbs still have flowers showing as late as mid December. This very early flowering is completely natural, and not as a result of forcing in any way.

Fruit pods: These are pale green (149D) when swollen after flower senscence. They are 10 mm in length, and 5–6 cm in diameter when complete, and contain between 30–50 small ½ mm white seeds. I do not know whether these seeds are fertile, as I have not tried to grown them from seed, but believe that they are fertile.

Propagation: This variety propagates well in that it produces on average two new bublets per season on a young bulb. It was initially multiplied from 5000 plants grown from tissue culture, and it took three seasons in a mild outdoor climate for the plants to reach flowering size. Subseqently, all propagation (asexual reproduction) has been by 'chipping' (cutting) the bulb into quarter segments and planting these chips. These chips take two seasons to reach a full sized flowering bulb. This Narsissus 'Charles Thatham' has been asexually reproduced exclusivly in the Island of Jersey, Channel Islands, UK. It has bred true to type consistantly,and is a stable cultivar.

PEST AND DISEASE RESISTANCE

This Narsissus species has good resistance to Narsissus eel worm and basal rot, moderate resistance to Narsissus fly species, and moderate to poor resistance to Narsissus Scorch (Stagonospora). No other pest or disease problems have been observed to date. More specifically, during the past 8 years of multiplication of this plant the following observations by me are:

1. Seasonally, only 2–4% of bulbs contained Narsissus fly damage, indicated during chipping.

2. To date there has been no recorded incidence of Narsissus eel worn seen by the States of Jersey Agricultural Inspectors on regular crop and bulb inspections.

3. The leaf disease 'Stagonospora' has been at between 5–20% of leaf area on unsprayed areas by the end of the season, just before leaf senescence. This variation is dependant on the climatic conditions seasonally that are condusive to its spread. Basal rot has only been seen in a dozen bulbs over the past 5 years.

I claim:

1. A new and distinct variety of *Narsissus tazetta* plant, substantially as herin described and shown as being exceptionally early in autumn flowering and uniquely winter hardy, and being different in floral colour and shape than any other outdoor autumn/late winter flowering *N. tazetta* such as Soliel D'or or White Narsissus to which it most closely resembles.

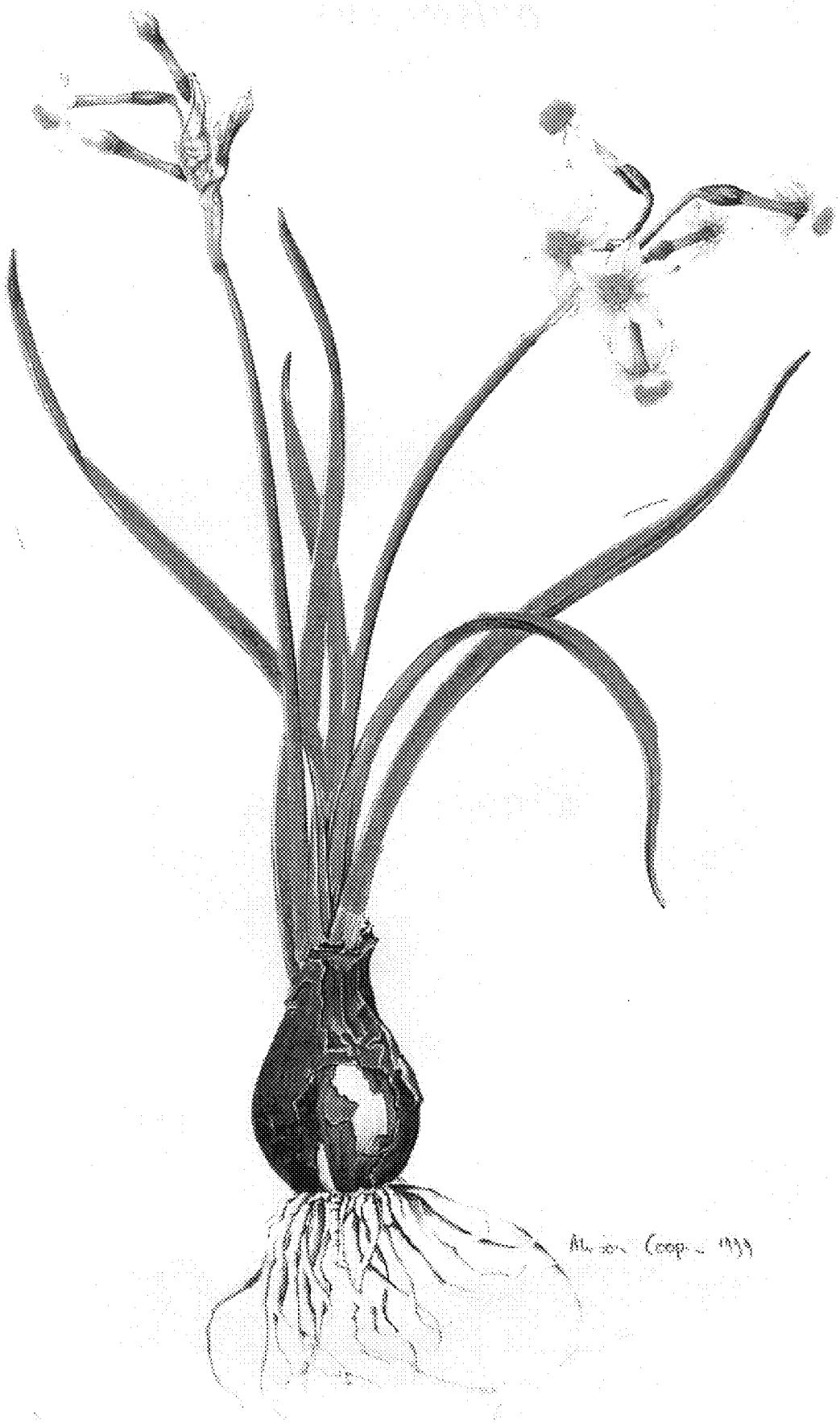

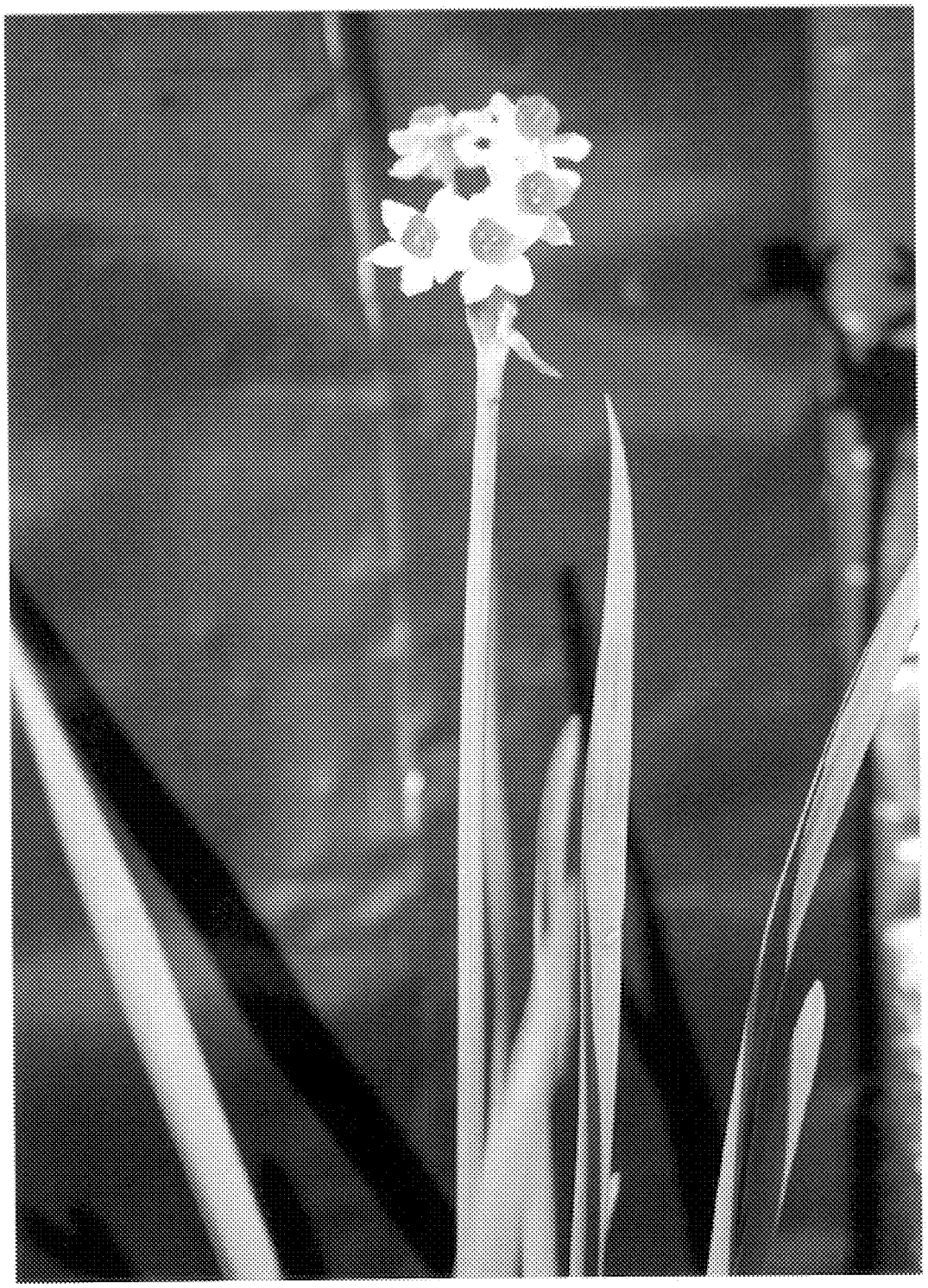

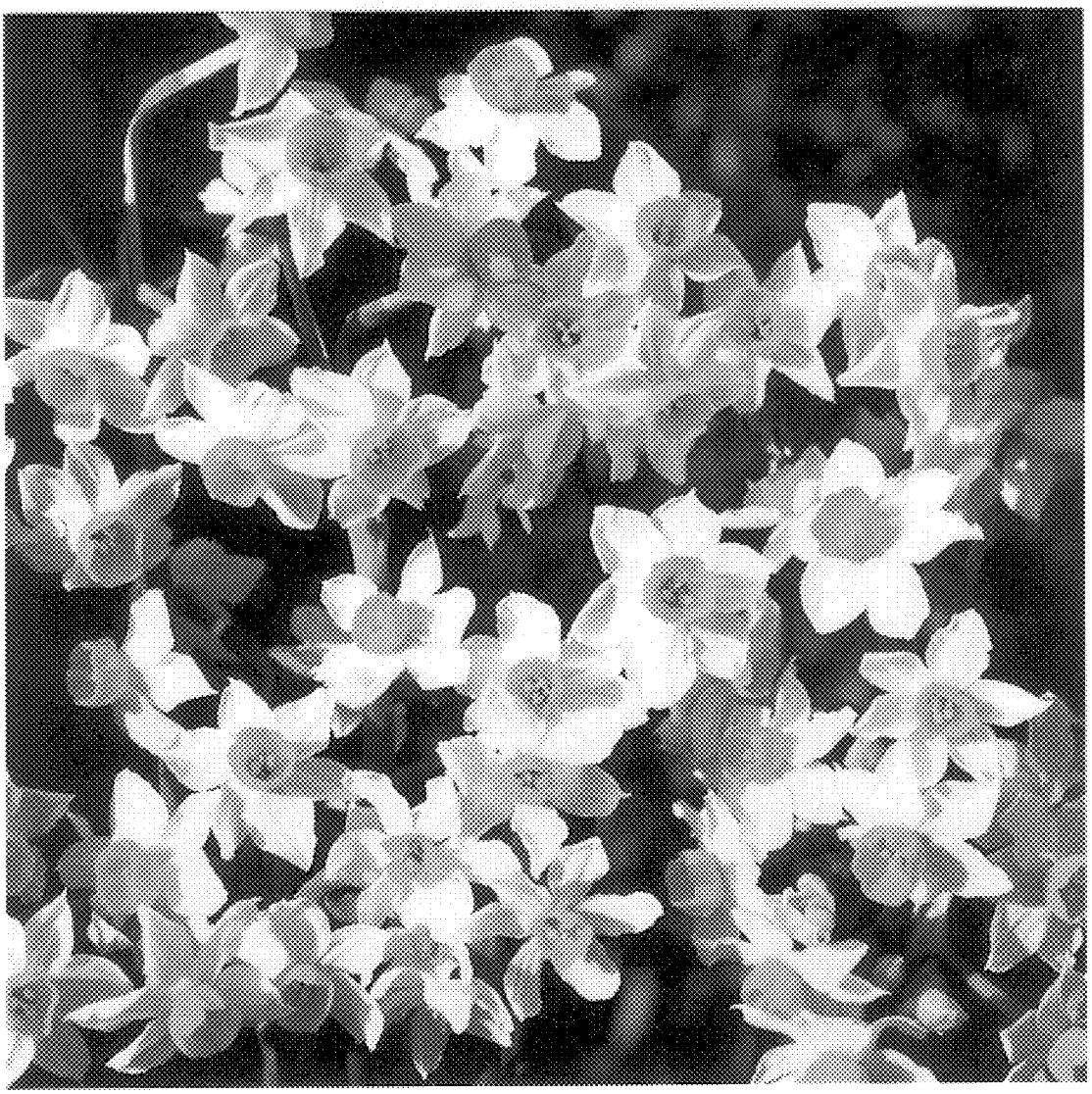

* * * * *